United States Patent [19]
Jiles et al.

[11] Patent Number: 5,313,405
[45] Date of Patent: May 17, 1994

[54] SYSTEM AND METHOD FOR NON-DESTRUCTIVE EVALUATION OF SURFACE CHARACTERISTICS OF A MAGNETIC MATERIAL

[75] Inventors: David C. Jiles; Levent B. Sipahi, both of Ames, Iowa

[73] Assignee: Iowa State University Research Foundation, Inc., Ames, Iowa

[21] Appl. No.: 754,904

[22] Filed: Sep. 4, 1991

[51] Int. Cl.$^5$ ................................................ G01B 7/24
[52] U.S. Cl. .................................... 324/209; 324/240; 364/486
[58] Field of Search ............... 324/202, 209, 227, 232, 324/252, 223, 260, 261, 262, 263, 240; 364/484, 486, 480

[56] References Cited

U.S. PATENT DOCUMENTS

| | | | |
|---|---|---|---|
| Re. 19,600 | 6/1935 | Hermann | 175/183 |
| 1,925,872 | 9/1933 | Hermann | 175/183 |
| 2,656,714 | 10/1953 | Cartier | 73/67 |
| 2,912,642 | 11/1959 | Dahle | 324/34 |
| 3,184,963 | 5/1965 | Dahle | 73/88.5 |
| 3,365,660 | 1/1968 | Steingroever | 324/34 |
| 3,427,872 | 2/1969 | Leep et al. | 73/88.5 |
| 3,706,029 | 12/1972 | Wandling et al. | 324/40 |
| 3,925,724 | 12/1975 | Steingroever | 324/34 R |
| 4,048,851 | 9/1977 | Portier | 73/141 A |
| 4,083,002 | 4/1978 | Allport | 324/227 |
| 4,138,783 | 2/1979 | Portier | 29/606 |
| 4,207,520 | 6/1980 | Flora et al. | 324/238 |
| 4,316,146 | 2/1982 | Jilken | 324/209 |
| 4,408,160 | 10/1983 | King et al. | 324/209 |
| 4,449,095 | 5/1984 | Steingroever et al. | 324/223 |
| 4,481,470 | 11/1984 | Wallace | 324/228 |
| 4,497,209 | 2/1985 | Kwun et al. | 73/601 |
| 4,523,482 | 6/1985 | Barkhoudarian | 73/862.36 |
| 4,599,563 | 7/1986 | Tiitto et al. | 324/232 |
| 4,623,841 | 11/1986 | Stinson et al. | 324/223 |
| 4,648,041 | 3/1987 | Tarr | 364/481 |
| 4,689,558 | 8/1987 | Ruuskanen et al. | 324/209 |
| 4,692,701 | 9/1987 | Dundas et al. | 324/240 |
| 4,745,809 | 5/1988 | Collins et al. | 73/661 |
| 4,746,858 | 5/1988 | Metala et al. | 324/200 |
| 4,788,504 | 11/1988 | Blanpain et al. | 324/377 |
| 4,792,756 | 12/1988 | Lam et al. | 324/232 |
| 4,855,677 | 8/1989 | Clark, Jr., et al. | 324/238 |
| 4,881,030 | 11/1989 | Stuecker et al. | 324/209 |
| 4,931,730 | 6/1990 | Olsen et al. | 324/209 |
| 5,008,621 | 4/1991 | Jiles | 324/227 |
| 5,117,184 | 5/1992 | Allison et al. | 324/239 |
| 5,164,669 | 11/1992 | Namkung et al. | 324/209 |
| 5,166,613 | 11/1992 | Perry | 324/209 |

FOREIGN PATENT DOCUMENTS 447653 4/1975 U.S.S.R.
532067 10/1976 U.S.S.R.
883827 11/1981 U.S.S.R.

OTHER PUBLICATIONS

Bozorth, "Ferromagnetism," Van Nostrand, New York, 1951, pp. 8, 9, 507, 512, 549 and 612.

(List continued on next page.)

*Primary Examiner*—Thomas G. Black
*Assistant Examiner*—Susan Wieland
*Attorney, Agent, or Firm*—Leydig, Voit & Mayer, Ltd.

[57] ABSTRACT

A system and a related method for non-destructive evaluation of the surface characteristics of a magnetic material. The sample is excited by an alternating magnetic field. The field frequency, amplitude and offset are controlled according to a predetermined protocol. The Barkhausen response of the sample is detected for the various fields and offsets and is analyzed. The system produces information relating to the frequency content, the amplitude content, the average or RMS energy content, as well as count rate information, for each of the Barkhausen responses at each of the excitation levels applied during the protocol. That information provides a contiguous body of data, heretofore unavailable, which can be analyzed to deduce information about the surface characteristics of the material at various depths below the surface.

12 Claims, 5 Drawing Sheets

OTHER PUBLICATIONS

Jiles, "The Effect of Compressive Plastic Deformation on the Magnetic Properties of AISI 4130 Steels With Various Microstructures," J. Phys. D: Appl. Phys. 21 (1988) pp. 1-9.

Jiles, "Variation of the Magnetic Properties of AISI 4140 Steels With Plastic Strain," Physicas S. Solidi, pp. 417-429 (Jun. 1988).

Jiles, "Integrated On-Line Instrumentation for Simultaneous Automated Measurement of Magnetic Field, Induction, Barkhausen Effect, Magnetoacoustic Emission, and Magnetostriction," J. Appl. Phys. 63(8), 15 Apr. 1988, pp. 3946-3948.

Jiles et al., "Theory of Ferromagnetic Hysteresis (Invited)," J. Appl. Phys. 55(6), 15 Mar. 1984, pp. 2115-2120.

Jiles et al., "Theory of the Magnetisation Process in Ferromagnets and its Application to the Magnetomechanical Effect," The Institute of Physics 1984, pp. 1265-1281.

Jiles et al., "Theory of Ferromagnetic Hysteresis," Elsevier Science Publishers B. V., 1986, pp. 48-60.

Garikepati et al., "Theory of Ferromagnetic Hysteresis: Evaluation of Stress From Hysteresis Curves," Center of NDE Iowa State University, Ames, Iowa 50011, No Date.

SYSTEM AND METHOD FOR NON-DESTRUCTIVE EVALUATION OF SURFACE CHARACTERISTICS OF A MAGNETIC MATERIAL

FIELD OF THE INVENTION

This invention relates to non-destructive evaluation, and particularly to a system and method for accurately and efficiently determining surface characteristics of magnetic materials.

BACKGROUND OF THE INVENTION

Magnetic inspection techniques provide an interesting alternative to more traditional non-destructive evaluation techniques of ultrasonics, eddy currents and radiography. They are of interest because of their perceived sensitivity to both stress and microstructure of the material. The possibility of usefully employing magnetic property measurements for materials evaluation has been known in principle for many years. However, although it was possible to demonstrate significant changes in the magnetic properties of materials as a result of thermal and mechanical treatment, the changes proved difficult to interpret because of their apparent complexity. For example, a given specimen subjected to the same external field, when also subjected to identical stress cycles, could exhibit changes in magnetization which were opposite in sign. Measurements could thus be made within a few minutes of each other with no apparent change in the external condition, but significantly different measurement results.

The Barkhausen effect is a magnetic effect, and Barkhausen effect evaluation fits within the broader category of magnetic inspection methods. The Barkhausen effect is postulated on small magnetic domains grouped together to form a larger magnetic sample. The domains are randomly distributed and positioned when the specimen is in a non-magnetic state. When a magnetic flux is applied to the material, the flux forces reorientation of the domains, and the domains are observed to shift suddenly. Shifting and change in domain size occur suddenly, creating magnetic responses, and the shifts occur at various depths in the material.

The Barkhausen effect can generate a relatively complex response characteristic. While researchers have studied the characteristic, the characteristic is so complex that it has not been possible heretofore to adequately analyze it in an efficient manner to derive very detailed properties on the characteristics of the sample which produced the result.

For example, it has been typical to detect the Barkhausen response then merely rectify or average it to produce a "Barkhausen number" which can then be compared to similar numbers for other samples. Other characteristics of the Barkhausen response may have been studied from time to time, but insofar as applicants are aware, means have not been available to accurately and reliably correlate information relating to the exciting or perturbing signal and multiple characteristics of the Barkhausen response. It has now been found that the ability to derive and correlate such information for a given excitation will allow the generation of significant detail on the structure of a magnetic sample at or near its surface, detail much more precise than has been available heretofore.

It has been learned that ferromagnetic materials exhibit hysteresis in the dependence of magnetization M on magnetic field H. As a result, the state of the system cannot be uniquely defined simply by external factors such as field strength and stress. A complete description of the system must include the prevailing magnetization and its history, and that information is not a single valued function of H and $\sigma$. However, insofar as applicants are aware, a system has not been available for controllably altering the field applied to a specimen whose surface characteristics are to be studied, for deriving adequate information including both frequency spectrum and amplitude information from the Barkhausen response in order to more completely utilize the Barkhausen response of the material to deduce material characteristics, and also to understand that response by virtue of knowledge of the fields and stresses which have been applied prior to the instant of measurement.

SUMMARY OF THE INVENTION

In view of the foregoing, it is a general aim of the present invention to produce an instrument and related procedure for generating and analyzing multiple aspects of Barkhausen response of magnetic material for detailed analysis of surface characteristics of the material.

In that regard, it is an object of the present invention to provide a system and related method for subjecting a magnetic sample to a time varying magnetic field, and for recording and analyzing multiple aspects of the complex Barkhausen response of the material in order to deduce surface characteristics thereof.

An object, according to the present invention, is to produce discontinuous changes in magnetic flux density B in a sample under test, then to perform a range of analysis procedures on those discontinuous changes with respect to both frequency and amplitude, in order to deduce details of the material properties not readily available heretofore.

According to a more detailed aspect of the invention, it is an object to perform a frequency spectrum analysis and a pulse height distribution analysis on the Barkhausen responses generated for multiple perturbing fields in order to deduce substantial detail of the surface characteristics of the material being tested.

According to a still more detailed aspect of the invention, an object is to controllably excite a magnetic material, detect the Barkhausen response of the material to that excitation, then to provide the capability for analyzing the frequency characteristic, amplitude characteristics, and average characteristics of the response in order to deduce more information with respect to the surface characteristics of the material than have been available from Barkhausen measurements performed heretofore.

A further object is to provide a system for rapidly and efficiently performing such analysis in an automatic fashion such that the excitation protocol applied to the material, and the Barkhausen responses to that excitation protocol are generated and detected respectively, for analysis and correlation of related data.

These and other objects and advantages will become apparent from the following detailed description when taken in conjunction with the drawings, in which:

DETAILED DESCRIPTION OF THE PREFERRED EMBODIMENTS

While the invention will be described in connection with certain preferred embodiments, there is no intent to limit it to those embodiments. On the contrary, the intent is to cover all alternatives, modifications and equivalents included within the spirit and scope of the invention as defined by the appended claims.

Figure 1:
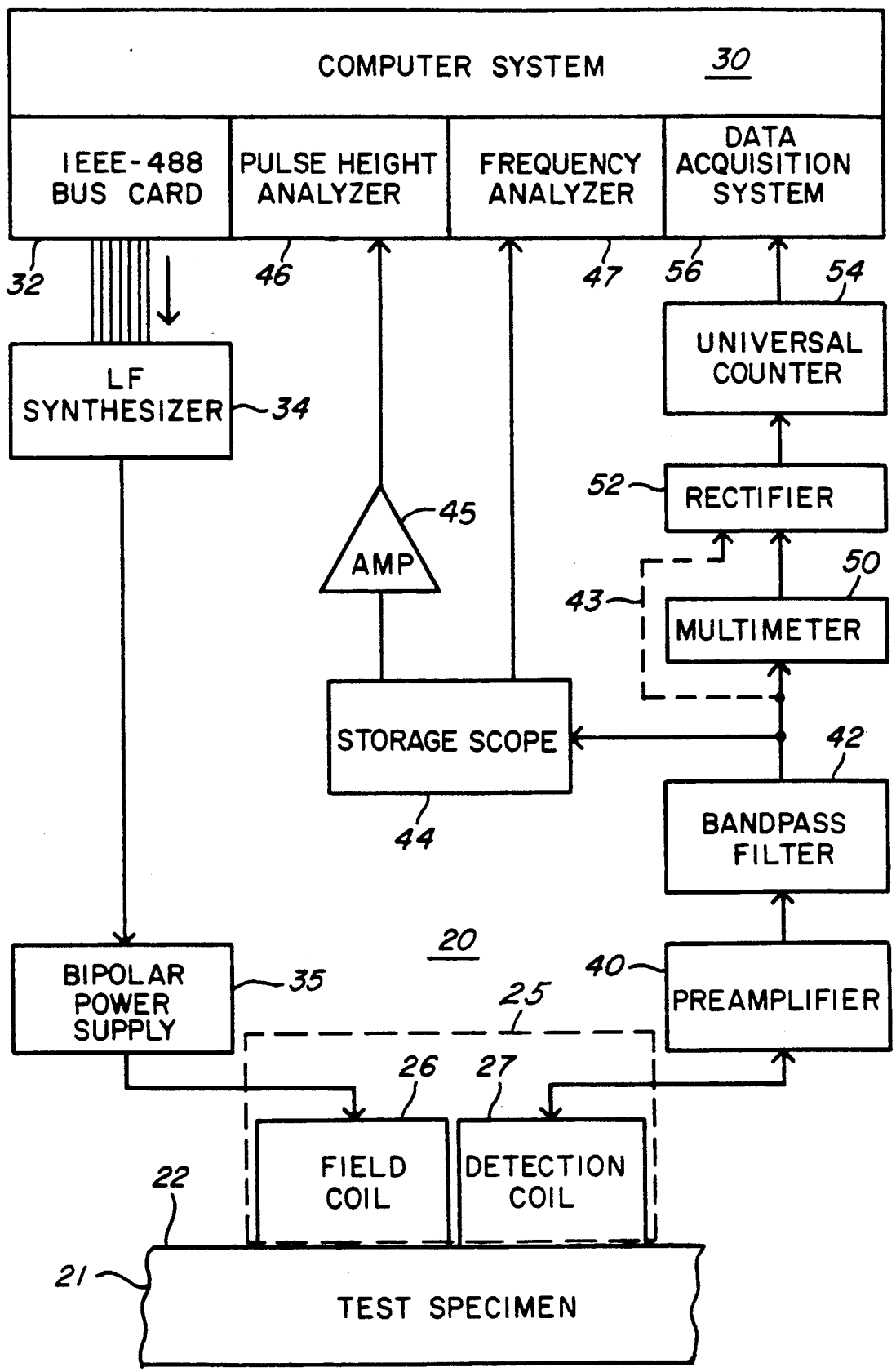
FIG. 1 is a block diagram illustrating a system for performing multiple aspect Barkhausen measurements and exemplifying the present invention.

Turning now to the drawings, FIG. 1 shows a system 20 capable of testing the surface characteristics of a test specimen or sample 21. The system operates by perturbing the specimen to produce discontinuous changes in magnetic flux density B in the specimen 21, then performing a range of analysis procedures on the complex signal in order to deduce details of the material property not readily available heretofore. In accordance with the present invention, such details of the material property are produced at or near the surface 22 of the test specimen 21 and, as will be described below, the sample 21 can be tested in such a way as to deduce characteristics of the sample at various controllable depths below the surface 22.

The instrument 20 includes probe means generally indicated at 25 including means 26, shown herein as a field coil, for exciting the sample and means 27, shown herein as a detection coil, for detecting the discontinuous changes in magnetization caused by the excitation. It is currently preferred to configure the probe means 25 as a coil or pair of coils wound directly on the test specimen, such coils achieving maximum coupling. However, it is desirable in many cases to utilize a probe means 25 which can be more readily brought into proximity with the test specimen 21 at one or more surfaces thereof, but without the need for winding a coil on the specimen itself. The probe means 25 of FIG. 1 is intended to be illustrative of both such probes.

In accordance with an important aspect of the present invention, the system 20 includes an intelligent controller, shown herein as computer system 30. In a practical implementation of the system, the controller 30 was an IBM PS/2 model 30/50 computer system with appropriate peripheral equipment to be described below. The computer system 30 allows the operator the ability to program an excitation protocol for the test specimen, and also to program the particular analysis to be performed on the Barkhausen emissions generated during the course of executing that protocol.

Coupled to the computer system 30 is a commercially available IEEE 488 bus card 32 which is a digital interface card adapted to respond to instructions from the computer system 30 to produce on an output bus 33 digital signals for control of external equipment. In the exemplary embodiment, the external equipment to be controlled is a low frequency synthesizer 34 such as the Philips Model PM5190. The low frequency synthesizer 34 responds to the digital outputs on bus 33 to produce signals which drive a bipolar power supply 35 which in turn produces excitation signals for the field coil 26. In a practical implementation of the present invention, the bipolar power supply is a Kepco BOP 50-8M. The power supply produces driving signals for the field coil 26 which establishes the repetition rate, amplitude and offset of the magnetic field applied to the test specimen 21 for excitation thereof.

In short, with respect to exciting the test specimen 21, the computer system 30 has the ability operating through interface lines 33 and the synthesizer/power supply combination to generate drive signals for the field coil 26 which produce a magnetic field having a controllable frequency, a controllable amplitude and a controllable DC offset. In addition, the DC offset can be varied with time to produce a further quasi-alternating aspect to the excitation signal.

In the currently preferred embodiment, the frequency synthesizer and bipolar power supply allow for a wide range of excitation frequencies which can control the depth of penetration of the magnetic field from approximately $10^{-2}$ meters to below $10^{-6}$ meters. On materials tested to date, excitation field frequencies in the range between about 30 and 150 Hz have been utilized, and the preference has been for operation of frequencies at about 30 Hz. It is worthy of note that the field excitation is applied at that frequency for a definite interval, in contrast to single DC field sweeps; the results produced with continuous alternating excitation have shown much cleaner output signals. In addition, the ability to operate under complex magnetic field excitation, which involves the superposition of an AC magnetic field on a prevailing DC magnetic field, as achieved by the system of FIG. 1, has been found to be significant. As noted above, the DC offset can also be a swept low frequency (quasi-DC) field to generate even further information.

The ability to understand and analyze the information generated by such complex excitation signals is an important aspect of the system 20 of FIG. 1. More particularly, the system, in addition to producing the complex excitation signal, analyzes the Barkhausen response with respect to frequency, amplitude and average information. The opportunity to extract all of that information concurrently from the same Barkhausen response or series of responses, as the field is excited according to a programmed protocol, will allow the analysis of data to deduce surface characteristics of the test specimen 21 not readily available heretofore.

Returning again to FIG. 1, the system 20 is seen to include elements coupled to the detection coil 27 which process the Barkhausen response for further analysis, then analyze the processed response to extract the needed information. To that end, a preamplifier 40 is fed by the detection coil 27, and the output of the preamplifier 40 feeds a bandpass filter 42. In a practical implementation of the system, the preamplifier is a PARC Model 113, and the bandpass filter a Krohn-Hite Model 3202. In normal operation, the bandpass filter is adjusted to pass all frequencies between 300 Hz. and 300 kHz. As will be described in greater detail below, it is sometimes useful to adjust the pass frequency of the filter 42 to produce additional useful information. It has been found that most of the useful Barkhausen signals occur between 200 kHz. and 300 kHz.

Figure 2:
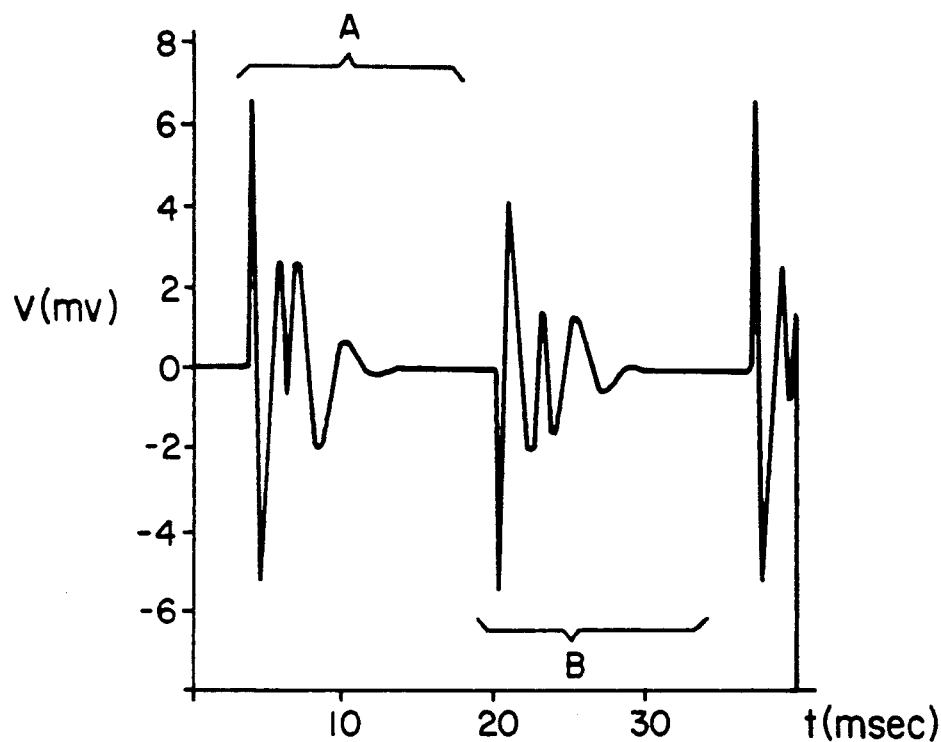
FIGS. 2 and 3 are diagrams illustrating the Barkhausen response of a given material at different applied field frequencies.
Figure 4:
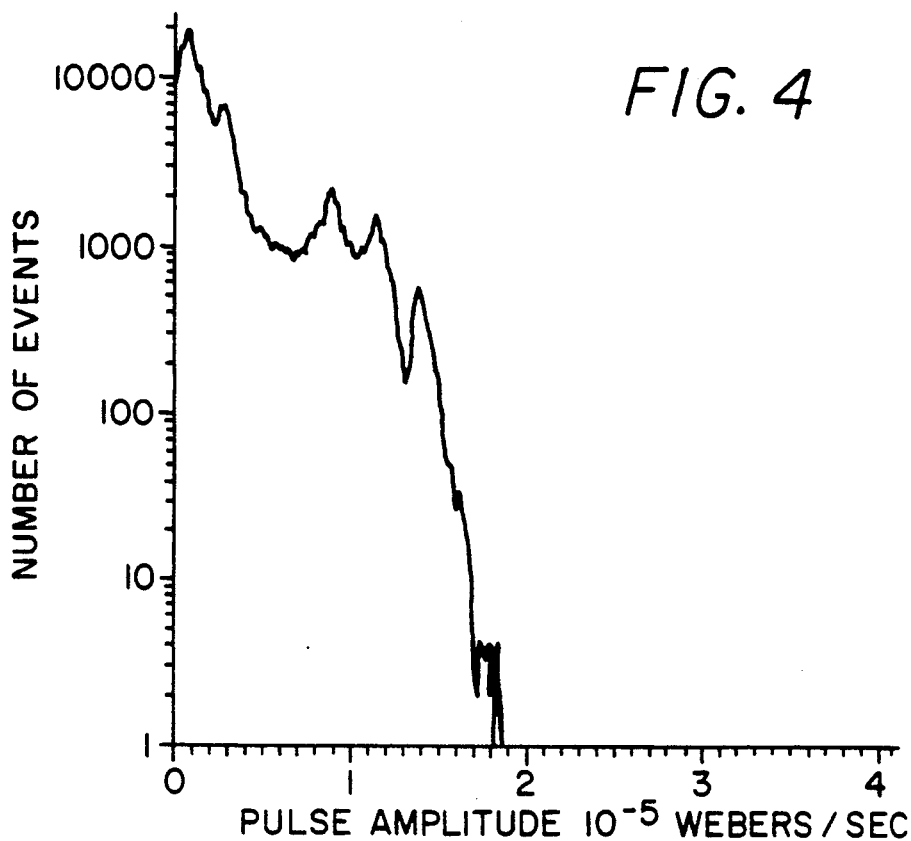
FIGS. 4 and 5 are pulse height histograms derived from Barkhausen responses of a given material excited at a given frequency and with different DC offsets.
Figure 5:
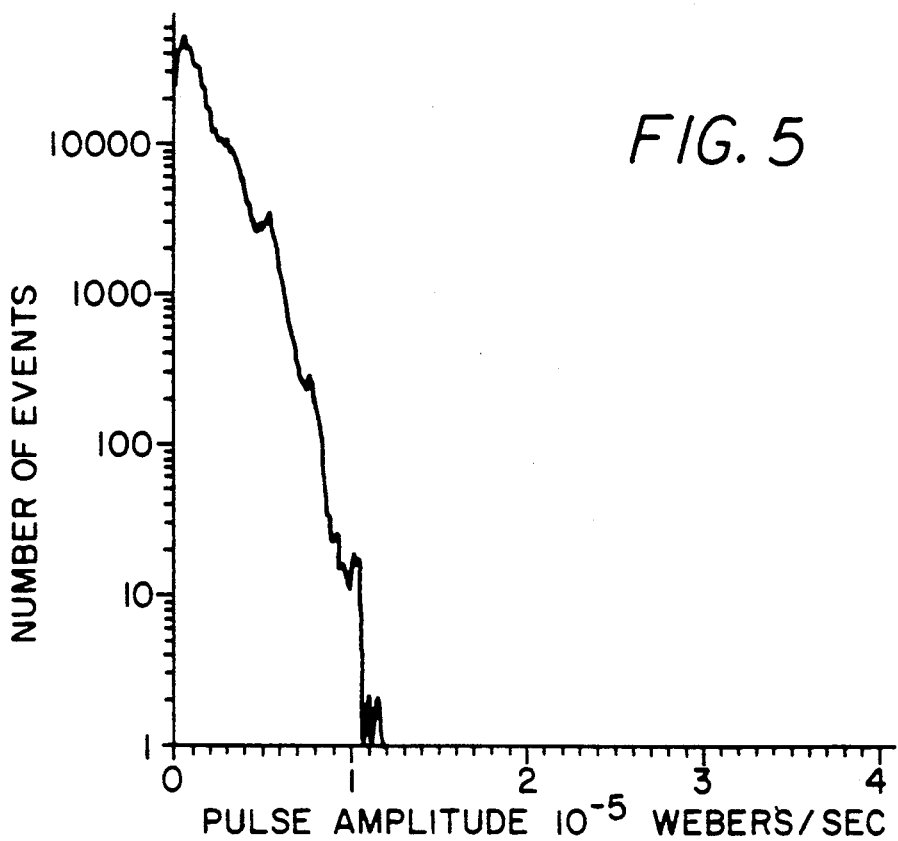

The frequency spectrum passed through the elements 40-42 then represents the Barkhausen response of the excited sample which is to be analyzed for further information. A storage oscilloscope 44 receives one branch of the output of the bandpass filter 42. The storage scope 44 is used as a mechanism for storing cycles of the Barkhausen response for further analysis. A typical form of Barkhausen response is illustrated in FIG. 2, which shows a complex waveform which repeats at the frequency of the applied magnetic field. The response has a characteristic which reverses with field reversals (apparently as a result of hysteresis) and which has various complex elements which will be described in detail below. With respect to field reversals, it is seen that the portion of the response bracketed at B is the mirror image of that bracketed at A and is due to the reversal of the 30 Hz. applied field. The Barkhausen response, after being amplified and filtered, is captured by the storage scope 44 in a manner represented by the illustration of FIG. 2, and is available for further analysis. In a practical implementation of the invention, the storage scope 44 is a Nicolet Model 3091. The signal is passed to analysis instrumentation controlled by the computer system 30 for pulse height and frequency analysis. With respect to pulse height, the signal from the storage scope 44 is passed through an amplifier 45 to a pulse height analyzer 46 which is controlled by the computer 30. The pulse height analyzer 46 then produces information, such as a histogram showing the distribution of pulses of various amplitudes within the complex Barkhausen spectrum stored on the storage scope 44. Examples of such histograms are shown in FIGS. 4 and 5.

In addition to analyzing the amplitude content of the complex signals stored in storage scope 44, the system 20 of FIG. 1 also analyzes the frequency information. To that end, an output of the storage scope 44 is coupled to a frequency analyzer 47 which is controlled by the computer system 30. The frequency analyzer produces information relating to the frequency content of the complex Barkhausen signal. Examples of such frequency related information are found in FIGS. 6 and 7 which show plots of the amplitude of the response in the Barkhausen signal as a function of frequency, and in effect show the energy content of the Barkhausen response present in each of the frequency bands of interest.

A final branch of measurement in the system 20 of FIG. 1 includes that capable of showing average energy in the Barkhausen response characteristic. To that end, a multi-meter 30 is coupled to the output of the bandpass filter 42. In a practical implementation of the invention, the multi-meter is a Hewlett-Packard Model 3457A, and is capable of measuring the RMS characteristic of a complex signal. That RMS signal, which is digital, can be passed directly to the computer system 30 for correlating with the other derived information a signal relating to average energy content of the Barkhausen response. As an alternative, the signal produced by multi-meter 30 can be passed to a rectifier 52 and a Universal counter 54 (such as a Hewlett-Packard 5316B) which produces count rate information for the pulses within the complex signal. That information is then passed to a data acquisition system element 56 controlled by the computer system 30. It is also possible, as suggested by dashed connection 43, to connect the input of the rectifier 52 directly to the output of the bandpass filter 42 to rectify the complex Barkhausen signal for application to the counter 54.

In summary, the computer system 30 is capable of generating complex excitation signals applied by way of field coil 26 to the test specimen. The Barkhausen response is detected by a detection coil 27. Each Barkhausen response is itself a complex waveform preamplified and filtered for further analysis. The system produces amplitude information via pulse height analyzer 46, frequency information via frequency analyzer 47, average signal content information by way of RMS multimeter 50, and count information via rectifier 52 and Universal counter 54. All of such information can be made available for each Barkhausen response, and as the computer causes the signal to sweep and change frequency or offset, the changes in those analyzed aspects of the Barkhausen criteria are also recorded and analyzed, which results in a cohesive body of information not heretofore available.

In short, for any given single Barkhausen response, there are four types of information which are generated, including amplitude information, frequency information, Barkhausen count rate information, and average information. The system utilizes a constant frequency AC excitation of the specimen to produce Barkhausen responses for the same excitation. The ability to excite the specimen at a constant frequency produces Barkhausen responses which are cleaner and less ambiguous for producing those four types of information. The computer then has the ability to alter the DC offset and note the changes in the four characteristics, to alter the applied AC signal and note the changes in the four characteristics, and also to program the protocol (AC excitation and DC offset or changes in DC offset) in accordance with the types of responses generated to the desires of the researcher.

The present invention is not directed to the particular data analysis techniques which can be applied to the derived signals. However, it is believed that armed with the present disclosure the researcher will be guided to numerous analysis techniques not available heretofore.

A significant aspect of the present invention is the provision of a correlated set of data which has not been available prior to this invention. Not only is a correlated set of data available for each Barkhausen response of a sample (that response being the characteristic response produced for a given AC excitation signal at a given offset). That response includes, as noted above, multiple attributes including amplitude, frequency, count rate and average. That information is enhanced by virtue of the constant AC excitation applied to the sample. However, having generated all of that information, the computer then has the capability of altering the AC excitation signal, the DC offset or slowly varying the DC offset, all of which produce altered Barkhausen responses in one or more of the four characteristics. The opportunity to capture all of those characteristics in conjunction with the altered excitation of the sample produces a body of correlated information which can be analyzed to produce information on the characteristics of the specimen at various depths at or below the surface 22 thereof.

The sample 21 can also be physically stressed while being tested, or altered such as by various mechanical processes between Barkhausen tests, and the ability to generate the extensive and correlated Barkhausen data for each iteration of the test will allow the researcher the ability to study in detail the nature of the specimen at or just below its surface.

Figure 3:
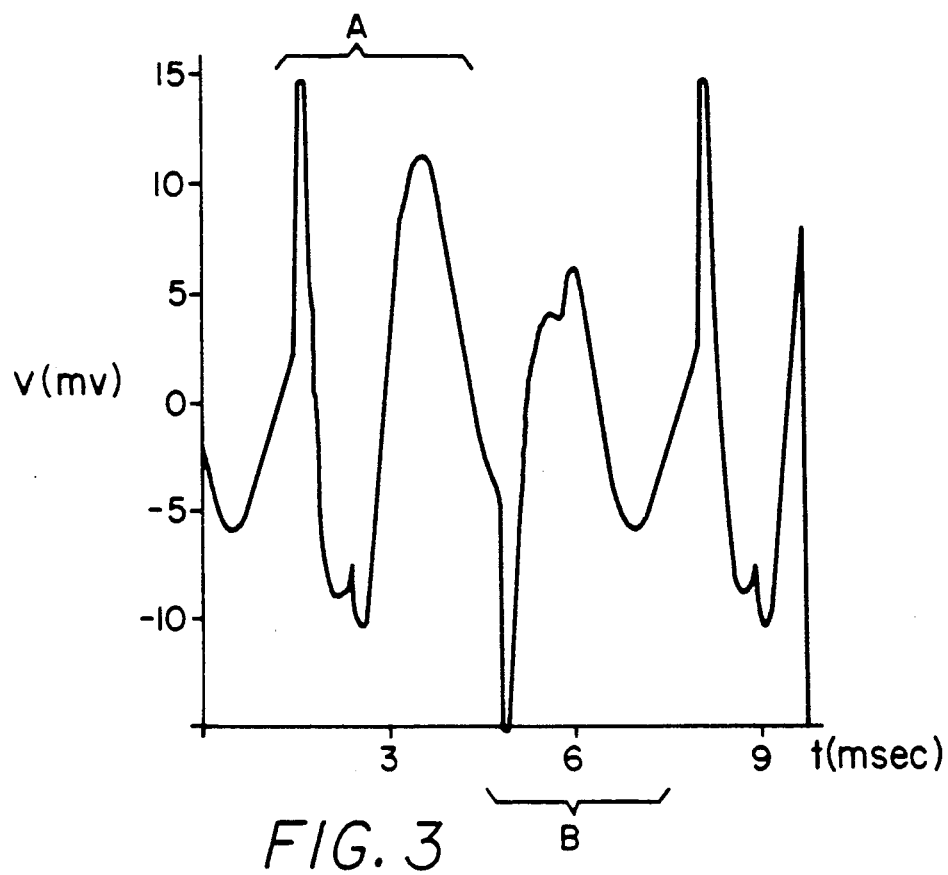

Referring now to FIGS. 2 and 3, there are shown the Barkhausen emission characteristics of a particular material at different frequencies but with the same offset. The material tested to generate the results of FIGS. 2 and 3 was a polycrystalline nickel specimen of cylindrical shape with a diameter of 19 mm. and a length of 270 mm. The sample was subject to an AC excitation field of amplitude 22 kA/m at frequencies to be specified below with a zero DC field bias. The FIG. 2 specimen was subjected to a frequency of 30 Hz. whereas to produce the Barkhausen result of FIG. 3, the sample was subjected to an AC field of 150 Hz. In the tests which produced the plots of FIGS. 2 and 3, it will now be apparent that the different frequencies correspond to different depths of penetration of the exciting magnetic field. While the actual depth of penetration cannot adequately be determined from classical skin depth theory, it is estimated that the range of frequencies illustrated in FIGS. 2 and 3 the depth of penetration was approximately 1 and 5 mm., respectively.

FIGS. 2 and 3 illustrate that clear signals are detectible under the action of a continuously varying AC field as contrasted with the single DC field sweep which had been available heretofore. It will be appreciated that the illustration of FIGS. 2 and 3 is that which is captured on the storage scope 44 of FIG. 1. The continuing refresh produced by the scope under conditions of constantly varying field sharpen the signal as will be apparent from FIGS. 2 and 3. It is seen that alternate pulse waveforms (A and B) are mirror images, one of the other (reflected in $V=0$ voltage axis), which is an interesting result since these waveforms correspond to the ascending and descending branches of the hysteresis loop.

It will also be apparent that while the FIGS. 2 and 3 results were produced with a DC field which was held constant, advantages can be gained in some instances by slowly sweeping a quasi-DC field to describe a hysteresis loop, and measuring the Barkhausen emissions generated by the AC field as a function of DC field strength. This, for example, would enable the coercivity of the material to be estimated.

FIGS. 4 and 5 show the distribution of pulse heights of the Barkhausen emissions at the same AC excitation field but at different DC offsets. FIG. 4 represents a pulse height histogram in the aforementioned polycrystalline nickel sample under an excitation H of 280 Oe, at a frequency of 30 Hz. with an applied DC field of 150 Oe. FIG. 5 represents the same material tested under the same AC excitation but with a DC offset of 200 Oe. It will be clear from results such as FIGS. 4 and 5 that the number of Barkhausen events at any given amplitude decreases as the DC offset field level is increased. However, the higher amplitude Barkhausen emissions are reduced more significantly than the low amplitude emissions as the DC offset field is increased.

Certain tests have indicated a continuum of Barkhausen pulse height amplitudes from effectively zero up to a maximum pulse height of about $1.8 \times 10^{-5}$ Webers per second. Some structure was apparent in the spectrum at about $1.4 \times 10^{-5}$ Webers per second. As a general characteristic, it was found that the larger the Barkhausen amplitude, the lower the frequency of the emission.

Figure 6:
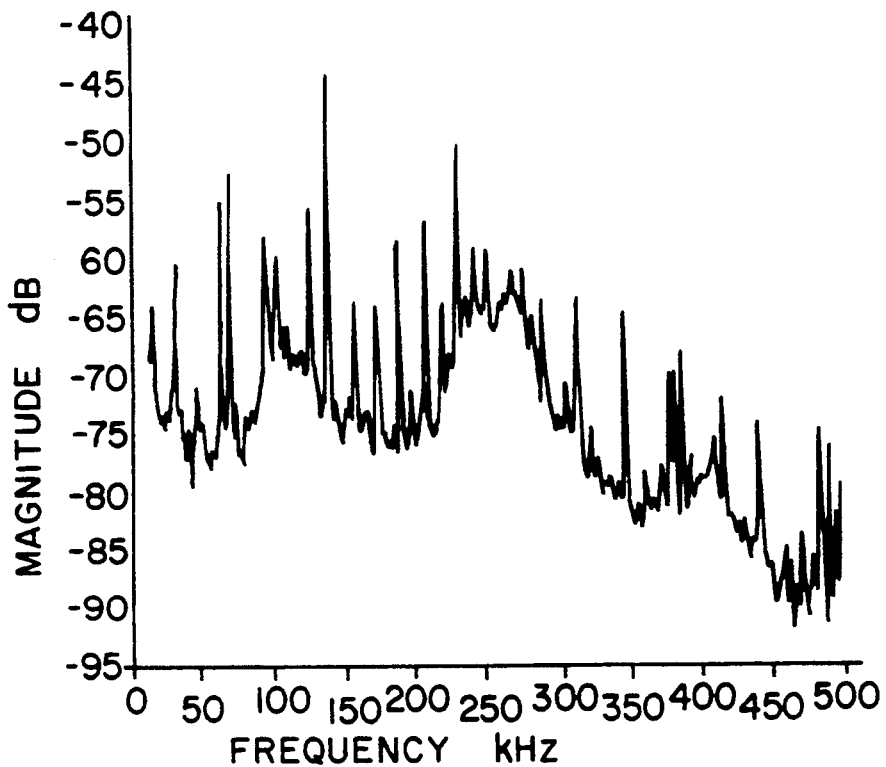
FIGS. 6 and 7 are frequency spectrums of Barkhausen responses of a given material excited at a given frequency and with different DC offsets.
Figure 7:
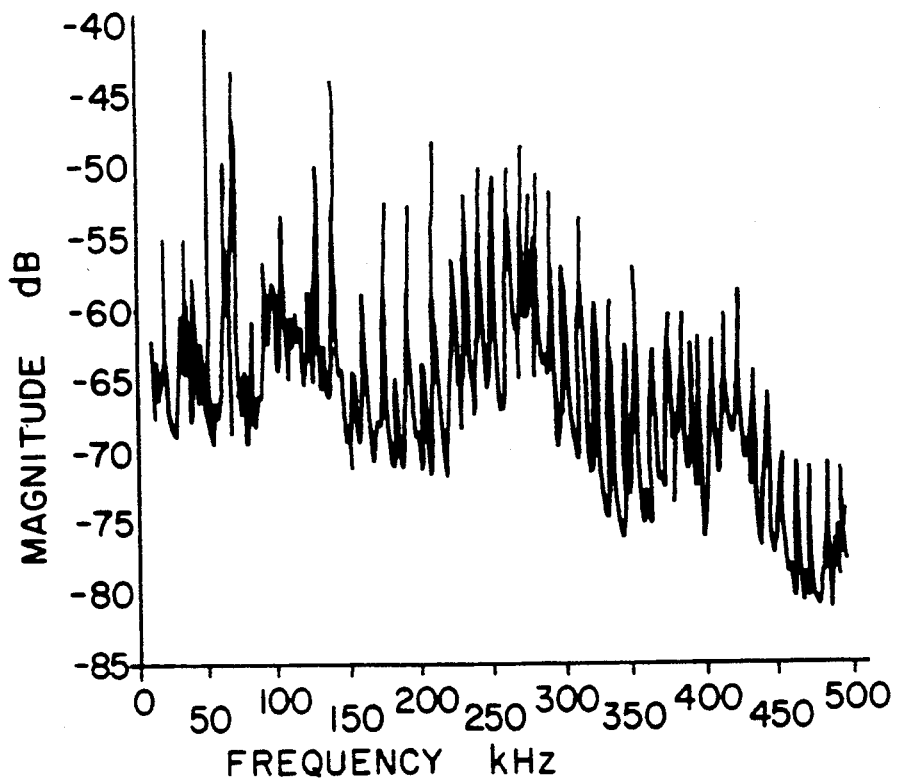

As noted above, the system also produces frequency information. Characteristic frequency information is illustrated in FIGS. 6 and 7. FIG. 6 illustrates the frequency spectrum of Barkhausen emissions in the aforementioned polycrystalline nickel sample under an AC excitation of 280 Oe at a frequency of 30 Hz. with an applied DC field of 0 Oe. FIG. 7 illustrates the result of the same sample at the same AC excitation and frequency but with a DC offset of 150 Oe. These results indicate a number of high amplitude narrow frequency range pulses which can be interpreted as the emissions due to individual domain walls which are excited with characteristic frequency. These high amplitude signals are superimposed on lower amplitude broad background spectrum. However, repetition of the measurements at a later time indicates that the broad background spectrum remains essentially the same while the narrow frequency high amplitude signals are significantly different. This seems to confirm the interpretation that the narrow frequency components of the spectrum are due to individual domain wall movements which could be entirely different from one run to the next. The broad background spectrum could be due to rotational processes. However, a comparison of FIGS. 6 and 7 taken at various times will clearly allow the deduction of surface characteristics of the tested material and the conditions to which it is subjected, in a way which has not been available heretofore.

Figure 8:
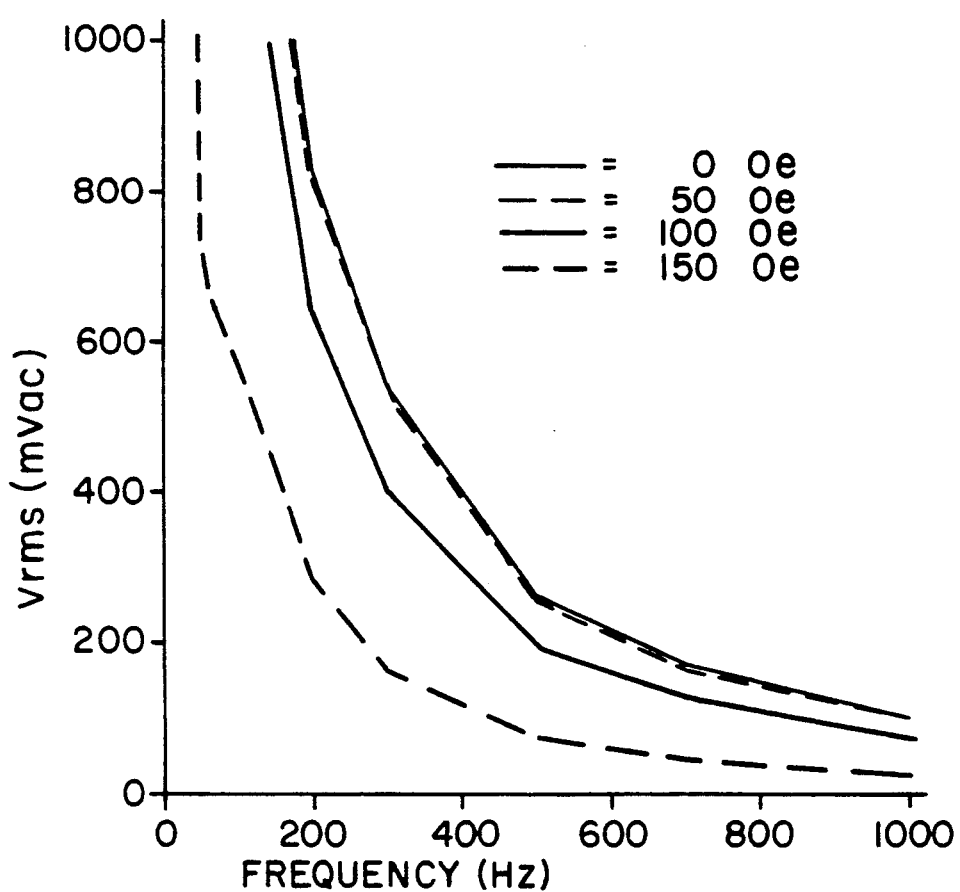
FIG. 8 is a plot illustrating the variation of RMS Barkhausen voltage with cutoff frequency for a given material excited at a given frequency and at different DC offsets.

Finally, FIG. 8 shows rectified or root mean square information derived from the system of FIG. 1. This is a simple and convenient measurement to make, requiring only the digital voltmeter with the capability of measuring RMS characteristics of voltages at various and complex frequencies. The response of FIG. 8 was generated by varying the cutoff frequency of the bandpass filter 42 (FIG. 1) to raise the cutoff frequency from 20 Hz. up to about 1K Hz. The result was continuously plotted as the frequency was raised to produce the characteristic shown in FIG. 8. The sample tested for the result of FIG. 8 was the same as that tested for the earlier plots, at an AC excitation of 280 Oe at a frequency of 30 Hz. The DC field offset for the various plots were 0 Oe, 50 Oe, 100 Oe and 150 Oe, respectively. Thus, the different depths of the material are examined, in which the maximum depth from which an emission can originate is limited by its observed frequency. The higher the frequency, the smaller the depth from which the response could have originated.

It will now be apparent that what has been provided is a system and a related method capable of generating related information which is relatively straightforward to analyze and which is derived from a relatively complex Barkhausen response. The individual responses are reliably generated in that they are produced by continuous application of an AC varying excitation signal at a constant frequency. Having generated a set of data for a given frequency, which includes both amplitude and frequency information as well as average information, the excitation frequency or offset are then altered to generate additional sets of responsive data, all of which are available for analysis to produce information relating to the specimen being tested. The opportunity to vary the AC field or the DC offset, and the generation of the individual amplitude, frequency and average signals from that information allows the relatively complex data which is generated to be selectively analyzed for information which had originated from various depths within the material. Thus, the sample can be tested to selectively determine information relating to the characteristics at the very surface of the sample or at selected depths below the surface.

With respect to data analysis, the intent of this specification is simply to show exemplary techniques for the analysis to illustrate the extreme utility of the system. The invention itself, however, resides in the ability to produce reliable Barkhausen responses, detect and segregate the amplitude, frequency and average characteristics from those responses at any given frequency, then to vary the frequency or offset and collect further sets of data all of which can be analyzed or correlated against each other or the excitation protocol (or the applied stress protocol, for example) to produce information on the sample which simply has not been available heretofore.

What is claimed is:

1. A system for producing information characterizing the properties of a sample of magnetic material near the surface of the sample comprising, in combination:

probe means magnetically coupled to the sample for (a) imposing a magnetic field on the sample and (b) detecting the magnetic response of the sample, energizing means driving the probe means for applying an alternating magnetic field at a plurality of frequencies selected to excite Barkhausen domains at different levels near but below the surface of the sample, detecting means coupled to the probe for detecting a complex magnetic Barkhausen response of the sample for more than one frequency selected to excite the Barkhausen domains, and processor means coupled to said energizing and detecting means for analyzing the characteristics of the respective detected complex Barkhausen responses at the applied frequencies to isolate at least frequency and amplitude information from each said response for determination of the surface characteristics of the magnetic sample excited by the alternating frequencies.

2. The system as set forth in claim 1 wherein the detecting means includes a pulse height analyzer and a frequency analyzer for analyzing the amplitude and frequency, respectively, of the Barkhausen response.

3. The system as set forth in claim 2 further includes means for averaging the Barkhausen response to produce an RMS measure of the Barkhausen response at the applied frequencies.

4. The system as set forth in claim 2 further including means for analyzing the count rate of the Barkhausen response at the applied frequencies.

5. The system as set forth in claim 2 further including storage means coupled to receive and store at least one complete period of the Barkhausen response, the pulse height analyzer and frequency analyzer being coupled to the storage means for analysis of the stored Barkhausen response.

6. The system as set forth in claim 2 further including a bandpass filter interposed between the probe means and the storage means for selectively passing a desired band width of the Barkhausen response for analysis.

7. The system as set forth in claim 2 wherein the driving means includes a low frequency synthesizer and a bipolar power supply controllably driven to apply a given driving magnetic field protocol to the probe means for exciting the sample according to the predetermined protocol.

8. A method of deriving information characterizing the properties of a sample of magnetic material near the surface of the sample, the method comprising the steps of:

(a) coupling a magnetic field having predetermined characteristics to the sample to excite Barkhausen domains therein;

(b) detecting the complex magnetic Barkhausen response from the excited sample for each period of the applied field;

(c) analyzing the complex Barkhausen response to extract at least frequency and amplitude information of the response for analysis to determine the surface characteristics of the magnetic sample excited by the applied magnetic field;

(d) varying the applied exciting field by controllably altering one or more of the characteristics of the field; and (e) repeating steps (b) and (c) at each applied exciting field to deduce surface characteristics of the sample at respective levels below the surface.

9. The method as set forth in claim 8 wherein the step of analyzing includes performing a pulse height analysis of the Barkhausen response to produce a histogram of the pulse height content of the Barkhausen response.

10. The method as set forth in claim 9 wherein the step of analyzing includes performing a frequency analysis of the Barkhausen response to isolate the frequency content of the pulses within the Barkhausen response.

11. The method as set forth in claim 10 wherein the analyzing step includes averaging each Barkhausen response to produce an RMS measure of said response at each applied frequency.

12. The method as set forth in claim 11 wherein the analyzing step includes analyzing the count rate of the Barkhausen response.

* * * * *

UNITED STATES PATENT AND TRADEMARK OFFICE
CERTIFICATE OF CORRECTION

PATENT NO. : 5,313,405
DATED : May 17, 1994
INVENTOR(S) : David C. Jiles and Levent B. Sipahi It is certified that error appears in the above-indentified patent and that said Letters Patent is hereby corrected as shown below:

Column 1, line 4,

This invention was made with Government support under Contract No. W-7405-ENG-82 awarded by U.S. Department of Energy. The Government has certain rights in the invention. --

Signed and Sealed this

Sixth Day of September, 1994

Attest:

BRUCE LEHMAN

*Attesting Officer*    *Commissioner of Patents and Trademarks*